(12) United States Patent
Pendekanti et al.

(10) Patent No.: US 6,415,179 B1
(45) Date of Patent: Jul. 2, 2002

(54) METHOD AND APPARATUS FOR IMPROVING THE PROBABILITY OF SUCCESS OF DEFIBRILLATION SHOCKS

(75) Inventors: Rajesh Pendekanti, Sunnyvale, CA (US); Patrick D. Wolf, Durham, NC (US)

(73) Assignees: Pacesetter, Inc., Sunnyvale, CA (US); Duke University, Durham, NC (US)

( * ) Notice: Subject to any disclaimer, the term of this patent is extended or adjusted under 35 U.S.C. 154(b) by 0 days.

(21) Appl. No.: 09/684,693

(22) Filed: Oct. 4, 2000

Related U.S. Application Data

(62) Division of application No. 09/212,033, filed on Dec. 14, 1998, now Pat. No. 6,154,672.
(60) Provisional application No. 60/090,248, filed on Jun. 22, 1998.

(51) Int. Cl.$^7$ .................................................. A61N 1/39
(52) U.S. Cl. ........................................................ 607/5
(58) Field of Search .................... 607/4, 14, 5; 600/518

(56) References Cited

U.S. PATENT DOCUMENTS

| | | |
|---|---|---|
| 5,161,528 A | 11/1992 | Sweeney |
| 5,500,008 A * | 3/1996 | Fain ................................ 607/5 |
| 5,545,189 A | 8/1996 | Fayram |
| 5,709,710 A | 1/1998 | Armstrong |
| 5,713,924 A | 2/1998 | Min et al. |
| 5,797,967 A | 8/1998 | KenKnight |
| 5,855,592 A | 1/1999 | McGee et al. |
| 5,865,838 A | 2/1999 | Obel et al. |

FOREIGN PATENT DOCUMENTS

| | | | | |
|---|---|---|---|---|
| WO | WO 99/47206 | 9/1999 | ............ | A61N/1/39 |
| WO | WO 99/47207 | 9/1999 | ............ | A61N/1/39 |

OTHER PUBLICATIONS

Charles D. Kirchhof, et al.; "Regional Entrainment of Atrial Fibrillation Studied by High–Resolution Mapping in Open–Chest Dogs"; Circulation, vol. 88, No. 2, Aug., 1993, pp. 736–749.

Maurits Wijffels, et al.; "Atrial Fibrillation Begets Atrial Fibrillation A Study in Awake Chronically Instrumented Goats"; Circulation, vol. 92, No. 7, Nov. 1995, pp. 1954–1968.

Walter Paladino, et al.; "Failure of Single–and Multisite High–Frequency Atrial Pacing to Terminate Atrial Fibrillation"; American Journal of Cardiology, vol. 80, 1997, pp. 226–227.

(List continued on next page.)

*Primary Examiner*—George R. Evanisko
(74) *Attorney, Agent, or Firm*—Steven M. Mitchell

(57) ABSTRACT

A system and method for providing improved defibrillation thresholds. In one embodiment of the invention, following the detection of fibrillation, a pacing pulse train is applied to a pacing electrode placed in the low gradient region of the left ventricular freewall to capture the tissue. In one embodiment, a pacing rate of about 80–95% of the VF cycle length is applied to achieve capture. Once capture of the tissue of the critical region is achieved, a high energy shock is delivered when the captured tissue is in the process of activation. The defibrillation shock is delivered at the end of the pacing train, with a coupling interval of either about 80–95% of the pacing rate (i.e., about 64–90% of the VF cycle length), or, alternatively, about 5–20% of the pacing rate (i.e., about 4–19% of the VF cycle length). In an alternative embodiment of the invention, a sensing electrode array is placed in the low gradient region of the left ventricular freewall to monitor such time as a substantial percentage of the tissue of the low gradient region is in the process of activation, i.e., on the downstroke of the respective EGMs, and then delivering the defibrillation shock at that instant.

4 Claims, 9 Drawing Sheets

OTHER PUBLICATIONS

Maurits Allessie, et al.; "Regional Control of Atrial Fibrillation by Rapid Pacing in Conscious Dogs" *Circulation*, vol. 84, No. 4, Oct., 1991, pp. 1689–1697.

Davy J., et al., "The relationship between successful defibrillation and delivered energy in open–chest dogs: reappraisal of the "defibrillation threshold" concept"; *Am Heart J.*, 1987; 113:77–84.

Souza et al., "Comparison of upper limit of vulnerability and defibrillation probability of success curves using a nonthoracotomy lead system"; *Circulation*, 1995, 91:1247–1252.

Chen, P., et al., "Comparison of activation during ventricular fibrillation and following unsuccessful defibrillation shocks in open–chest dogs"; *Circ Res.*, 1990;66:1544–1560.

Zhou, X., et al., "Epicardial mapping of ventricular defibrillation with monophasic and biphasic shocks in dogs"; *Circ Res.*, 1993;72:145–160.

Walcott, G., et al., "Mechanisms of defibrillation for monophasic and biphasic waveforms"; *PACE*, 1994;17:478–498.

Swartz, J., et al., "The conditioning prepulse of biphasic defibrillator waveforms enhances refractoriness to fibrillation wavefronts"; *Circ Res.*, 1991;68:438–449.

Dillon, S., et al., "Optical recordings in the rabbit heart show that defibrillation strength shocks prolong the duration of depolarization and the refractory period"; *Circ Res.*, 1991;69:842–856.

Dillon, S., et al., "Synchronized repolarization after defibrillation shocks—A possible components of the defibrillation process demonstrated by optical recordings in rabbit heart"; *Circulation*, 1992;85:1865–1878.

\* cited by examiner

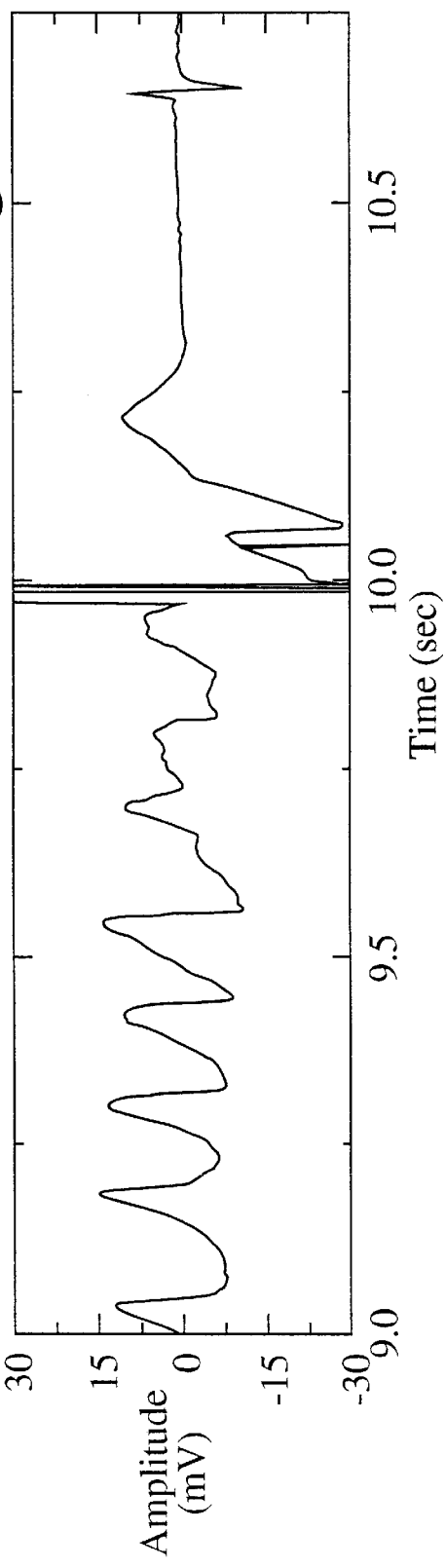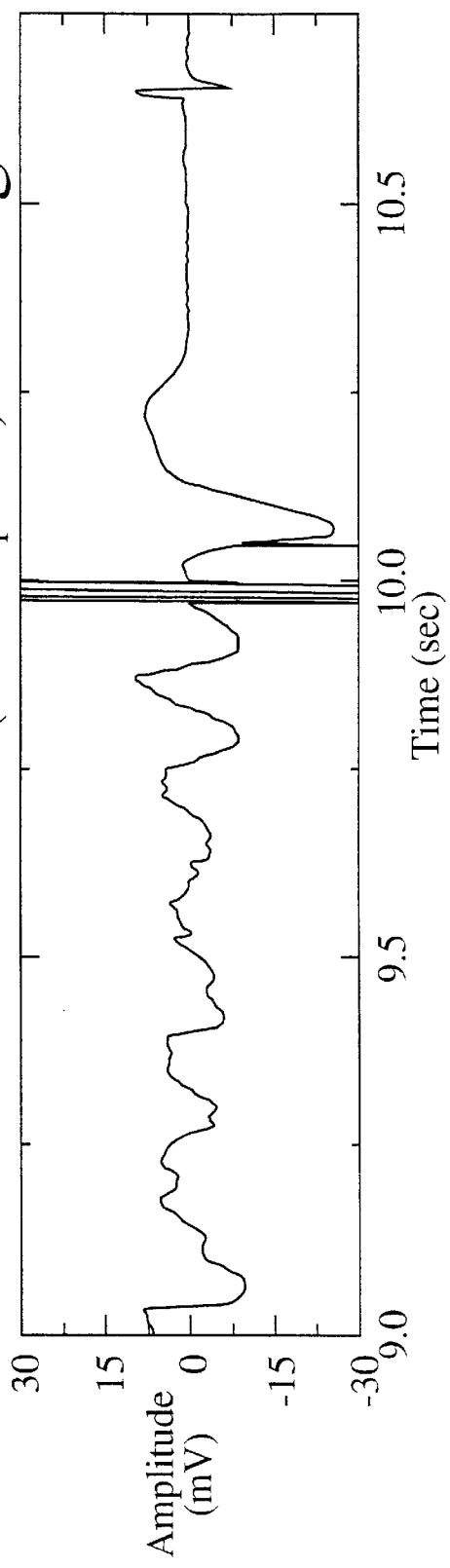

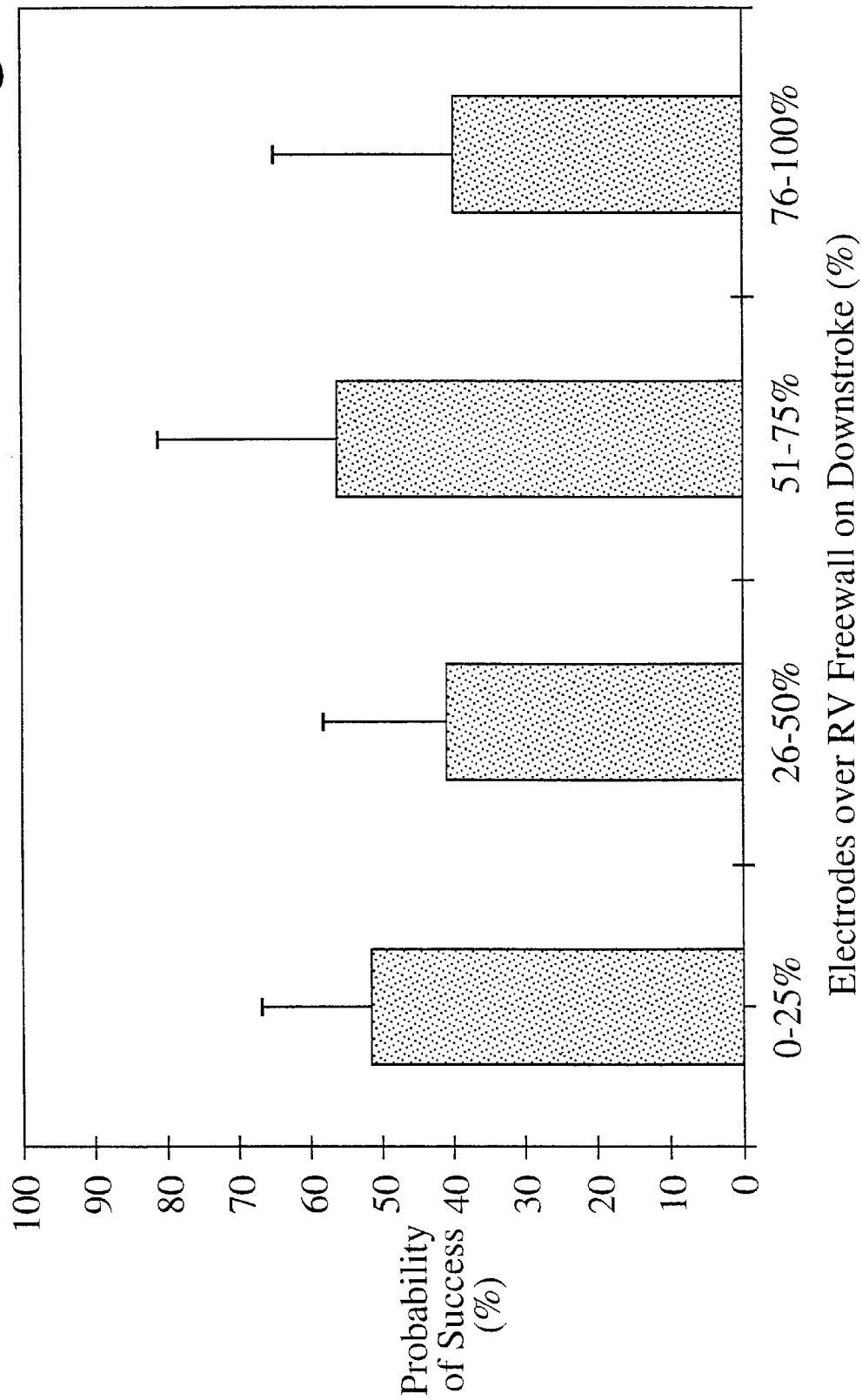

METHOD AND APPARATUS FOR IMPROVING THE PROBABILITY OF SUCCESS OF DEFIBRILLATION SHOCKS

This is a divisional of application Ser. No. 09/212,033, filed on Dec. 14, 1998. Now U.S. Pat. No. 6,154,672.

CROSS-REFERENCE TO RELATED APPLICATIONS

This application claims the benefit of U.S. Provisional Application No. 60/090,248, filed Jun. 22, 1998.

BACKGROUND OF THE INVENTION

This invention relates generally to implantable defibrillators and more particularly to a method and apparatus for providing more efficient ventricular defibrillation shocks.

Cardiac arrhythmias can generally be thought of as disturbances of the normal rhythm of the heart muscle. Cardiac arrhythmias are broadly divided into two major categories, bradyarrhythmia and tachyarrhythmia. Tachyarrhythmia can be broadly defined as an abnormally rapid heart (e.g., over 100 beats/minute, at rest), and bradyarrhythmia can be broadly defined as an abnormally slow heart (e.g., less than 50 beats/minute). Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular. In general, atrial arrhythmias are non-life threatening, chronic conditions, because the atria (upper chambers of the heart) are only responsible for aiding the movement of blood into the ventricles (lower chambers of the heart), whereas ventricular arrhythmias are life-threatening, acute events, because the heart's ability to pump blood to the rest of the body is impaired if the ventricles become arrhythmic. This invention is particularly concerned with treatment of ventricular fibrillation.

Since an individual who experiences fibrillation typically will not always be immediately accessible by emergency care technicians and their equipment, and/or will become incapacitated and unable to beckon such care, implantable cardiac stimulation devices have become critical delivery systems of emergency care for many patients with chronic heart failure problems.

Various types of implantable cardiac stimulation devices are presently available and used for delivering various types of cardiac stimulation therapy in the treatment of cardiac arrhythmias. The two most common types which are in widespread use are pacemakers and implantable cardioverter defibrillators (ICDs).

Pacemakers generally produce relatively low voltage pacing pulses which are delivered to the patient's heart through low voltage, bipolar pacing leads, generally across spaced apart ring and tip electrodes thereof which are of opposite polarity. These pacing pulses assist the natural pacing function of the heart in order to prevent bradycardia.

On the other hand, ICDs are sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle. In general, an ICD continuously monitors the heart activity of the patient in whom the device is implanted by analyzing electrical signals, known as electrograms (EGMs), detected by sensing electrodes positioned in the patient's heart. More particularly, contemporary ICDs include waveform digitization circuitry which digitizes the analog EGM produced by the sensing electrodes, and a microprocessor and associated peripheral integrated circuits (ICs) which analyze the digitized EGM in accordance with a diagnostic algorithm implemented by software stored in the microprocessor. Contemporary ICDs are generally capable of diagnosing the various types of cardiac arrhythmias discussed above, and then delivering the appropriate electrical stimulation/therapy to the patient's heart, in accordance with a therapy delivery algorithm also implemented in software stored in the microprocessor, to thereby correct or terminate the diagnosed arrhythmias. Typical electrical stimulus delivery means used in ICDs involve an energy storage device, e.g., a capacitor, connected to a shock delivering electrode or electrodes. Contemporary ICDs are capable of delivering various types or levels of electrical therapy. U.S. Pat. No. 5,545,189 provides a representative background discussion of these and other details of conventional ICDs, and the disclosure of this patent is herein incorporated by reference.

One conventional method of electrical shock therapy for treating ventricular arrhythmia is to deliver a single burst of a relatively large amount of electrical current through the fibrillating heart of a patient by an ICD supported-electrode configuration installed in or about the patient's heart. For a given ventricular fibrillation episode, the minimum amount of energy required to defibrillate a patient's ventricle is known as the ventricular defibrillation threshold (VDFT). However, in the treatment of an acute cardiac condition, such as ventricular fibrillation, conventional ICD-based therapies have encountered a dilemma in that while higher strength defibrillation shocks generally have a higher probability of success of achieving defibrillation than lower strength shocks, the countervailing consideration is that higher energy shocks demand commensurately greater ICD equipment capabilities and cost, such as in terms of batteries, capacitors, and so forth.

It has been experimentally observed that the likelihood of successful defibrillation has been shown to follow a sigmoidal shaped curve in which higher strength shocks have a higher probability of success than lower strength shocks. See, e.g., Davy J., et al., "The relationship between successful defibrillation and delivered energy in open-chest dogs: reappraisal of the "defibrillation threshold" concept," *Am Heart J*. 1987; 113:77–84. When a number of shocks are applied at the V50 level, 50% of applied shocks are expected to result in successful defibrillation. In order to interpret the increased probability of success in terms of percentage improvement in DFT, some previously published data is available to illuminate the issue. For a superior vena cava (SVC) lead and right ventricle (RV) lead configuration, for example, the probability of success curves have been developed to determine that (V80−V50)/V50=0.14. E.g., see Souza et al., "Comparison of upper limit of vulnerability and defibrillation probability of success curves using a nonthoracotomy lead system," *Circulation*, 1995, 91:1247–1252. By linear approximation of the central portion of the sigmoidal curve, this yields (V70−V50)/V50=0.09. This equation indicates that if the probability of success in achieving defibrillation at a certain voltage is 50%, then increasing the voltage by 9% will increase the probability of success to 70%.

Yet, the ICD device preferably should be designed to be as small in dimensions and light in mass as possible so as to be less cumbersome and bulky to the patient, so it generally will not be practical to significantly scale-up the power and voltage capabilities of an ICD device in many cases as the mode of increasing the probability of success in the delivery of defibrillation therapy.

Instead, it would be desirable to find ways to lower the VDFT for a given ICD size and power. Furthermore, a patient having an installed ICD may experience several or more acute separate fibrillation episodes a year requiring intervention by the installed ICD unit. Thus, it can be appreciated how lowering of the energy requirements demanded of the ICD would be desirable so as to prevent premature depletion of the batteries, and thereby increase the service life of the ICD device.

Also, while a patient experiencing a ventricular fibrillation episode, may or may not be conscious or semi-conscious, it is still possible that the patient could potentially perceive any programmed electrical stimulation treatment being performed on his/her heart during the episode. Thus, to mitigate any possible further trauma to the patient on account of any negative perceptions of the electrical jolts accompanying the VDF shocks, or, alternatively, to reduce the risk of inadvertent myocardial tissue damage from the delivered shock, it also would be desirable to reduce the ventricular defibrillation threshold (VDFT) for these additional reasons.

Thus, it is desirable for reasons of both increased device longevity and patient comfort/safety to reduce the amount of energy required to defibrillate a patient's heart when using an implantable cardioverter defibrillator (ICD). However, this goal had not previously been fully satisfied in the ICD field despite active interest and numerous experimental studies reported in the relevant field.

As generally known, during ventricular fibrillation (VF), it has been observed that shocks of the same voltage can at some times achieve successful defibrillation (DF), yet fail at other times. It has been observed that a factor contributing to this phenomena is that the electrophysiological state of cardiac tissue in the so-called "low gradient region" of the heart can exist in various conditions of depolarization and repolarization at various times.

The "low potential gradient region," or "low gradient region" for short, is that region of the heart tissue that is most remote from the defibrillation electrodes and thus experiences a lower electrical gradient relative to other portions of the heart at the time of delivery of a defibrillation shock. More specifically, the low potential gradient region thus is where the electric field lines generated by the current flowing between a pair of defibrillation electrodes positioned in the heart are the least densely spaced. The location of this region can vary to the extent that the potential gradients generated by a defibrillation shock depend upon the particular lead configuration of the defibrillation electrodes in the heart, the tissue conductivities, and torso geometry. The low potential gradient region can be located by measurement or intuitively.

Previous cardiac mapping studies have demonstrated that, following a failed defibrillation shock, the earliest sites of propagation from which post-shock activation wavefronts originate tend to appear from regions where cells are just emerging from their effective refractory period immediately prior to the defibrillation shock. See, e.g., Chen. P., et al., "Comparison of activation during ventricular fibrillation and following unsuccessful defibrillation shocks in open-chest dogs," *Circ Res.* 1990;66:1544–1560; Zhou, X., et al., "Epicardial mapping of ventricular defibrillation with monophasic and biphasic shocks in dogs," *Circ Res.* 1993;72:145–160; Walcott, G., et al., "Mechanisms of defibrillation for monophasic and biphasic waveforms," *PACE.* 1994;17:478–498.

Prior studies also have shown that these earliest sites of propagation are the regions where extracellular potential gradients are lower than a critical value. It follows from this that the shock strength in the low gradient region can be too low to cause any extension of refractoriness in the local tissue. Moreover, in the low gradient region, shocks can cause action potential stimulation only when they are applied very late in the repolarization phase. See, e.g., Swartz, J., et al., "The conditioning prepulse of biphasic defibrillator waveforms enhances refractoriness to fibrillation wavefronts," *Circ Res.* 1991;68:438–449; Dillon, S., et al., "Optical recordings in the rabbit heart show that defibrillation strength shocks prolong the duration of depolarization and the refractory period," *Circ Res.* 1991;69:842–856; Dillon, S., et al., "Synchronized repolarization after defibrillation shocks—A possible component of the defibrillation process demonstrated by optical recordings in rabbit heart," *Circulation.* 1992;85:1865–1878. These results have been interpreted to suggest that one possible factor contributing to the probabilistic character of defibrillation is that the state of repolarization of tissue in the low gradient region is different at different times.

Despite the improved understanding being developed in the field on the relationship of the electrophysiological characteristics of the low gradient region of the heart and efficacy of defibrillation therapy, there still exists a need for a modality of delivering cardiac therapy that improves the probability of success of a ventricular defibrillation shock while also reducing ventricular defibrillation thresholds (VDTs) to reduce energy demands placed upon an ICD device and to reduce the risk of pain, trauma or myocardial tissue damage to a patient undergoing defibrillation treatment.

The above and other objects, benefits and advantages are achieved by the present invention as described herein.

SUMMARY OF THE INVENTION

The present invention relates to treatment therapies and systems for ventricular arrhythmias which reduce ventricular defibrillation threshold (VDFT) energy requirements and/or increase the probability of a successful outcome when the defibrillation shock is delivered at a given energy level.

In one embodiment of the invention, VDFT energy requirements have been demonstrated to be dramatically reduced by delivering a pacing regimen to the low gradient region of the heart in conjunction with a timed-delivery of a defibrillation shock in synchronization to activation sensed in the low gradient region. More specifically, following the detection of fibrillation, one or several successive pacing pulse trains are applied to a pacing electrode placed in the low gradient region of the heart to capture the tissue. Once capture of a substantial extent of the tissue of the low gradient region is achieved via pacing, a high energy defibrillation shock is delivered in a timed manner. In one specific implementation of this embodiment, the location of the low gradient region is the left ventricular (LV) freewall, and a pacing rate of about 70–99%, and more preferably 80–95%, of the ventricular fibrillation cycle length (VFCL) sensed at the low gradient region is applied to achieve capture in the low gradient region. Then, a defibrillation shock is delivered at the end of the pacing train, preferably with a time interval between the last pacing pulse and the delivery of the defibrillation shock being a duration of time of either about 80–95% of the pacing rate or about 5–20% of the pacing rate. The timing of the delivery of the defibrillation shock preferably is based on information contained in electrogram signals acquired in real time from a sensing site at the low potential gradient during fibrillation.

One of the specific findings of the present invention is that the defibrillation shock has a greatly increased probability of success if a substantial majority of the tissue in the low gradient region is in the process of activation by fibrillatory wavefronts or is about to be depolarized. In the first-mentioned case, the depolarization caused by defibrillatory wavefronts is thought to add to the depolarization caused when the defibrillation shock is delivered, and in the latter case, the tissue around the electrode is thought to be at the end of its refractory period and will hence require a lower voltage gradient by the defibrillation shock to become depolarized. When pacino is used to achieve regional capture in the low gradient region, as described herein, the timing of the defibrillation shock will be caused to occur during either one of the above-mentioned electrophysiological periods by delivering the shock after the last pulse at an interval of about 80–95% of the pacing rate or about 5–20% of the pacing rate, respectively. This mode of tiered therapy effectively reduces the ventricular defibrillation threshold (VDFT) that otherwise would be applicable in the absence of the preliminary pacing tier of therapy.

As compared to VDFT without regional capture being provided via pacing prior to delivery of the defibrillation shock, the VDFT with regional capture provided via pacing in accordance with this embodiment of the invention is significantly lowered, which, in turn, significantly reduces the battery and energy requirements of an ICD or like device for defibrillation.

In an alternate mode of this invention, real time sensing in the low gradient region is used to generate ventricular electrogram (EGM) information from one or more sensing sites in the low gradient region, and when the sensed data indicates a substantial extent of tissue is simultaneously in the process of activation or is about to be depolarized, then the defibrillation shock is immediately delivered. This alternative mode of therapy involves "passive-timing" in the sense that no intervention effort is made to disturb the natural electrophysiological state of the heart with external electrical stimuli until one of several opportunistic electrophysiological states are detected as occurring in the myocardial tissues of the low gradient region. Namely, the indication that a substantial extent of myocardial tissue is in the process of activation or is about to be depolarized in the low gradient region, and thus is more likely to respond favorably to a defibrillation shock, has been found to be highly predictable by the occurrence and detection of certain electrophysiological states in the low gradient region.

In one implementation, it has been found that the amount of reduction achieved in the DFT energy, or, alternatively, the probability of a successful outcome when the defibrillation shock is delivered at a given energy level, increases as a direct positive function of the percentage of the low gradient region that is in downstroke when the defibrillation shock is delivered. In implementing this embodiment, where one sensor is monitored in the low gradient region, then the defibrillation shock is delivered when the EGM is in the downstroke. Where two or more separate sensors are monitored in the low gradient region, an initial monitoring period of, for example, about 2–4 seconds, is conducted in which a defibrillation shock is delivered when and if all electrograms are simultaneously determined to be on downstroke. If the initial monitoring period elapses without that occurring, then the defibrillation shock is delivered the next time a majority (>50%), and more preferably >80%, of the EGMs from the sensed sites are simultaneously on downstroke. This technique involves a binary classification of the slope of the EGM profile being monitored in real time as being on an upstroke (i.e., where the slope of the EGM curve is numerically positive in value) or downstroke (i.e., where the slope of the EGM curve is numerically negative in value). This approach increases the amount of tissue depolarized at the end of the defibrillation shock and thereby enhances the probability of reducing the VDFT.

In another implementation, besides the above-mentioned binary classification of slope method for timing the delivery of the defibrillation shock, it is also possible to reference other EGM quantities, such as the amplitude of the electrogram and the magnitude of the slope of the electrogram sensed from the low gradient region, and use these parameters instead for timing the delivery of the defibrillation shock. Namely, another finding of the present invention is that either a relatively large amplitude or a large negative slope observed at an electrogram from the low gradient region has been found to indicate the presence of a large and rapidly moving activation wavefront over the low gradient region, which in turn indicates an increased probability of a large percentage of low gradient region tissue being on the downstroke of its EGM. It has been found that immediately delivering the defibrillation shock when the magnitude of the downstroke is sensed to be relatively large in amplitude or negative slope value results in a increased probability of success of defibrillation. Moreover, there exists an increased probability of a lower VDFT being exploitable at that time.

In further embodiments of the present invention, there are systems provided for implementing the various above-introduced methods of the invention.

For purposes of this application, the following terms have the indicated meanings:

Capture: means pacing of the ventricle from one or more sites where each pacing stimulus results in a repeatable activation pattern of the entire ventricle. The wavefronts originate at the pacing electrodes and the phase relationship between the pacing stimulus and the activation of each section of the ventricular tissue remains constant throughout the pacing event.

Entrainment: means the same as capture.

Regional capture: pacing of the ventricle from one or more sites where the stimulus results in wavefronts which depolarize only a portion of the myocardium surrounding the electrode or electrodes. The spatial extent of the depolarization caused by the pacing stimulus changes from beat to beat and occasionally may result in almost no propagated response. The wavefronts activating the captured region originate at the pacing electrode. The phase relationship remains constant between the pacing stimulus and activation of each section of myocardium within the region that is captured.

Phase-locking: pacing of the ventricle from one or more sites which results in wavefronts that appear to be constant in phase with the pacing stimulus but where there does not appear to be a cause and effect relationship. That is, the wavefronts do not appear to originate at the pacing sites and small changes in phase between the pacing stimulus and the activation of each section of a region occur over time. As a qualification, where EGM data on the ventricle is limited, it is often difficult to differentiate between phase-locking and capture, as defined herein, and, for those cases, phase-locking terminology is used herein to refer to both capture and phase-locking.

"Ventricular Defibrillation Threshold" or "VDFT": The minimum amount of electrical energy required to defibrillate a fibrillating ventricle of a patient.

"Ventricular Fibrillation Cycle Length" or "VFCL", for short: the timing required between two consecutive depolarization wavefronts to traverse the same location is the ventricular fibrillation cycle length (VFCL).

"Pacing Rate": also referred to herein as the "S1-S1" interval, meaning the time intervals between delivery of successive pacing pulses.

"Coupling Interval for Pacing Initiation" or "CIPI", for short: means the time delay between the last local activation sensed, as the trigger, and the start thereafter of the first pulse of the pacing train.

"Coupling Interval for Defibrillation Shock" or "CIDS", for short: also referred to herein as the "S1-S2" interval, meaning the time interval between the last pulse of a pulse train and the specific time thereafter when a VDF shock, i.e., the defibrillation trigger, is delivered.

"Low potential gradient region of ventricular tissue" or "low gradient region" for short: the region in the heart, as described supra, where the electric field lines generated by the current flowing between a pair of defibrillation electrodes positioned in the heart are the least densely spaced. The location of this region can vary to the extent that the potential gradients generated by a defibrillation shock depend upon the particular lead configuration of the defibrillation electrodes in the heart, the tissue conductivities, and torso geometry. The low potential gradient region can be located by measurement or intuitively.

"Upstroke" and "downstroke" terminology herein relates to the electrogram morphology at each sensing electrode as being classified, respectively, as being on an "upstroke" when the slope of the electrogram (dV/dt) is greater than zero, and on a "downstroke" when the slope of the electrogram (dV/dt) is less than zero. Further, the upstroke and downstroke terminology will be understood to be a function of the polarity of the connections to the sensing amplifier. In this regard and for purposes of simplifying the descriptions herein, the upstroke and downstroke terminology are premised on the sensing electrodes being connected to the positive side of the sensing amplifier and the ground being connected to the negative side of the sensing amplifier. Of course, it will be appreciated that the polarity of the connections to the sensing amplifier could be switched from this arrangement and this disclosure then would still remain applicable by merely switching all present references herein of downstroke to upstroke, and vice versa.

BRIEF DESCRIPTION OF THE DRAWINGS

These and various other features and aspects of the present invention will be readily understood with reference to the following detailed description taken in conjunction with the accompanying drawings, in which:

FIG. 1A shows an epicardial electrogram for "electrode #1", which was among 525 simultaneously acquired epicardially electrograms during a VF/DF episode that is described in experimental section of this application.

FIG. 1B shows an epicardial electrogram for "electrode #5", which was another electrode location among the 525 simultaneously acquired epicardially electrograms during a VF/DF episode that is described in experimental section of this application.

FIG. 4 shows histograms similar to that shown in FIG. 3, except that the electrograms used were from the right ventricular free wall.

DETAILED DESCRIPTION OF THE PREFERRED EMBODIMENTS

When heart cells are activated, the electrical polarization caused by the normal voltage difference of about 90 mV between the inside and outside of the cells collapses and the heart tissue is said to "depolarize." Depolarized heart tissue which has not been given adequate time to re-establish its normal voltage difference and will not produce a new activation in response to a further intrinsic or extrinsic electrical stimulus is referred to as refractory tissue. After depolarization, heart cells begin to re-establish the normal voltage difference ("repolarization"). Tissue which has been afforded an adequate length of time to re-establish a sufficiently large voltage difference to once again become susceptible to depolarization is no longer refractory. The time interval which is required after a cell has been depolarized until it is again non-refractory is called the refractory period. In a fibrillating heart, depolarization wavefronts move through the myocardium along re-entrant pathways in a chaotic manner. The time period required for a given depolarization wavefront to traverse and complete a circuit along some re-entrant pathway in the ventricle is the ventricular fibrillation cycle length (VFCL). The period following an activation when tissue becomes non-refractory again is referred to as the "excitable gap." The present invention offers modes of cardiac therapy that overcome the challenges posed by the chaotic electrophysiological characteristics of a fibrillating heart.

MODE I: DEFIBRILLATION THERAPY WITH PACING TIER

In one mode of the present invention, a hybrid therapy is provided that uses pacing pulses for achieving regional capture of the low gradient region followed by delivery of a defibrillation shock to provide lower defibrillation thresholds (DFTs). Compared to VDF without capture, experimental studies summarized herein have shown that the VDFT energy required to terminate fibrillation with capture pursuant to the therapy regimen of this invention is significantly lower, viz. about 14 to 38% lower in power requirements, as demonstrated by studies in dogs with chronic VF.

Figure 6:
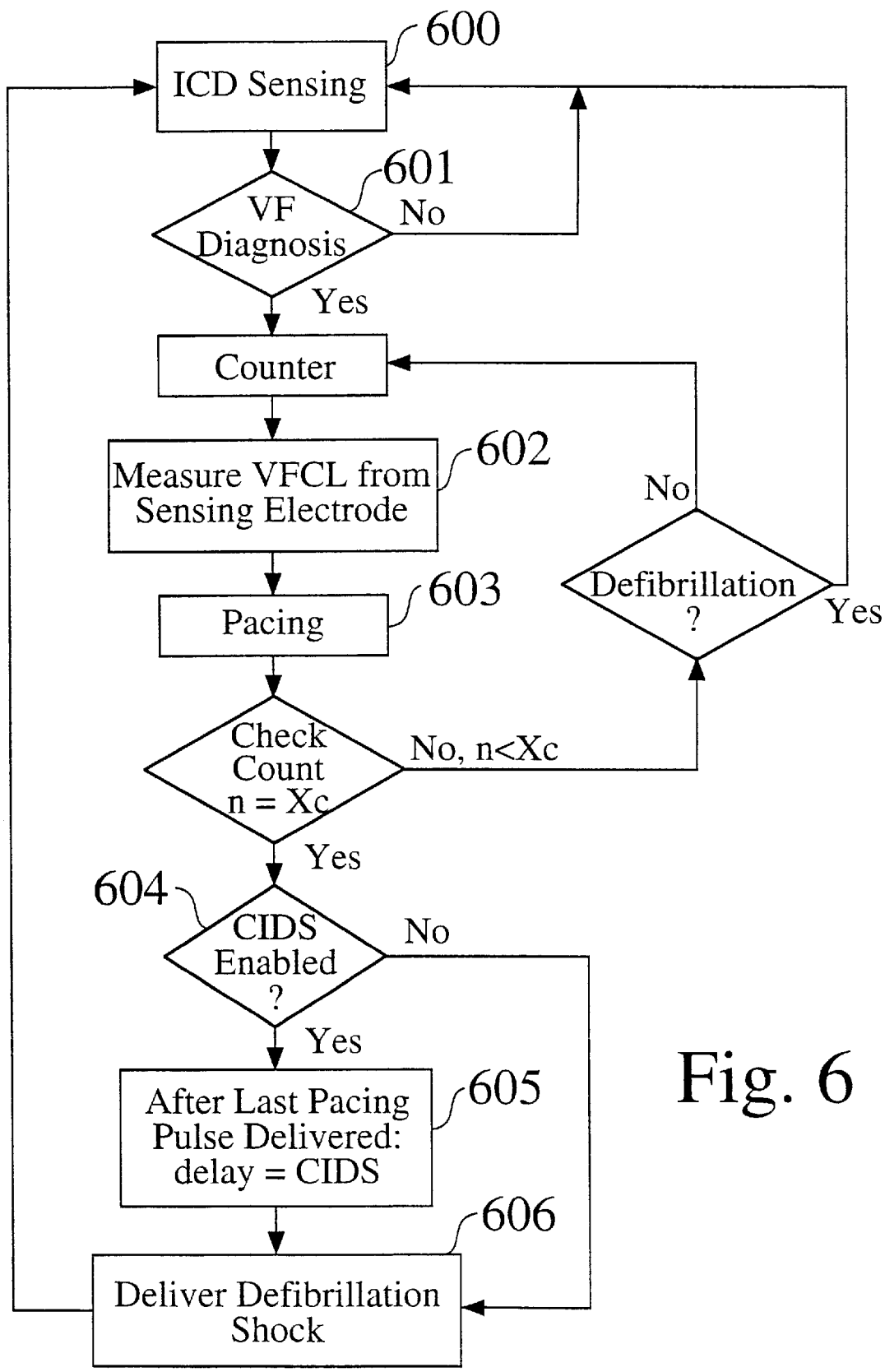
FIG. 6 is a flow chart illustrating a treatment method of the present invention involving tiered therapy for achieving ventricular defibrillation using pacing and defibrillation shocks.

As indicated in FIG. 6, delivery of pacing (603) is based on VFCL measurement (602) following initial VF diagnosis (601) from ICD sensing (600). The pacing is delivered at a pacing site that is adjacent to the low potential gradient region of ventricular tissue as an equal-interval train of pulses delivered at a predetermined coupling interval set proportional to a ventricular fibrillation cycle length (VFCL) value. The VFCL value can be determined by counting the number of depolarization wavefronts to enter the given ventricular site over a selected period time and then calculating the median or mean VFCL value from that information. For instance, to determine VFCL, the activation profile is sensed and monitored via EGM signals for a brief period of time, e.g., over several seconds (e.g., 1–2 seconds), at the site where pacing is to be delivered. The median or arithmetic mean VFCL value is calculated from the data collected at the sensed local site. It typically is preferable to calculate the median VFCL for a sensed local site to better attenuate any possible extreme outlying data points, although the mean VFCL values are also acceptable in most cases.

Based on the sensed VFCL data, the pacing is controlled in real time such that the Coupling Interval for Pacing Initiation (or CIPI), i.e., the time between the last activation sensed and the delivery of the first pulse of the pulse train, is selected so as to fall in the excitable gap. Thus, the CIPI is selected to be sufficiently long to ensure that the myocardial tissue is well out of refractoriness so that the local region to be paced can be easily excited by the first pulse of the respective pacing train, whereby the resulting wavefront spreads out rapidly at the pacing site to capture a large portion of the surrounding tissue. On the other hand, the coupling "S1-S1" interval is also selected to be shorter than the VFCL so that the pacing stimulus induced preemptively activates and depolarizes the tissue before the next fibrillation wavefront is expected to invade the area. Since depolarization wavefronts associated with fibrillation require repolarized tissue to propagate, depolarization wavefronts can be constrained in this manner. This provides the capture of the tissues surrounding the pacing site.

This pacing regimen brings large regions of fibrillating tissue in the low gradient region into capture (phase-lock) via delivery of pacing level pulses alone. Once capture is obtained via such pacing, a defibrillation shock is delivered to terminate fibrillation.

As a secondary tier (in time) of the VDF therapy, after the delivery of pacing effective to provide the aforesaid large-scale or regional capture of the tissue in the low gradient region, defibrillation shocks (S2) are delivered in timed intervals proportional to the pacing (S1-S1) interval to terminate the fibrillation.

In a preferred embodiment of this invention using the pacing regimen, the pacing train is delivered to the pacing site in the low gradient region to capture tissue at a CIPI and a uniform S1-S1 interval each proportionally set as about 70 to 99%, preferably about 80 to 95%, of the VFCL. Next, the defibrillation shock is delivered to terminate fibrillation at a uniform time interval between the last pulse of the pulse train and the specific time thereafter when the VDF shock is delivered (also referred to herein as the "S1-S2 interval"), as proportionally set as about 80 to 95% or, alternatively, about 5 to 20%, of the S1-S1 interval. Put another way, where S1-S1 is set to be in the range of about 80 to 95% of the VFCL, S1-S2 is set to be in the range of either about 64 to 90% of the VFCL, or 4 to 19% of the VFCL.

The desired significant reductions in the VDFT energy requirements are very sensitive to the S1-S2 interval value, and become readily lost as the S1-S2 interval goes below 5% of the S1-S1 interval, or goes to between approximately 20 to 85% of the S1-S1 interval, or goes above 95% of the S1-S1 interval. For example, if the S1-S1 interval is 100 milliseconds for a pulse train in an ongoing VDF treatment, then the S1-S2 interval (CIDS) preferably would be set to a value between 80 to 95 milliseconds, e.g., 90 milliseconds, or alternatively, to a value between 5 to 20 milliseconds, to satisfy the above-indicated criterion for selecting the S1-S2 interval (CIDS).

One of the specific findings of the present invention, as demonstrated in the examples herein, is that the defibrillation shock has a greatly increased probability of success if a substantial majority of the tissue in the low gradient region is in the process of activation by fibrillatory wavefronts or is about to be depolarized. While not desiring to be bound to any particular theory at this time, it nonetheless is thought that in the first-mentioned case, the depolarization caused by defibrillatory wavefronts is thought to add to the depolarization caused when the defibrillation shock is delivered, and in the latter case, the tissue around the electrode is thought to be at the end of its refractory period and will hence require a lower voltage gradient by the defibrillation shock to become depolarized. When pacing is used to achieve regional capture in the low gradient region, as described herein, the timing of the defibrillation shock will be caused to occur during either one of the above-mentioned electrophysiological periods by delivering the shock after the last pulse at an interval of about 80–95% of the pacing rate or about 5–20% of the pacing rate, respectively.

The sensing mechanism useful for collecting electrophysiological data on a fibrillating ventricle that is useful for determining local ventricular fibrillation cycle lengths according to the principles of this invention include those that are conventional in the art. Such sensors generally comprise a conventional sensing electrode or electrodes, positioned in or on the heart in locations suitable for monitoring the electrical activity associated with a fibrillating heart and producing analog electrocardiogram (EGM) signals in response thereto; an amplifier for amplifying the EGM signals; a waveform digitization means for digitizing the EGM signals to produce digital electrocardiogram (EGM) signals; and signal processing means that process the EGM data in accordance with the therapy delivery algorithm (implemented in software) embraced by this invention. For example, the signal processing means can be a microprocessor used for diagnosing whether fibrillation is present, determining the fibrillation cycle length(s), calculating the appropriate pacing and/or shock rates needed based on the VFCL data, and confirming whether fibrillation is terminated upon treatment. The determination of the fibrillation cycle length can be done by counting the number of depolarization wavefronts to enter the site being sensed over a fixed period time, e.g., several seconds, and then calculating the median or mean VFCL value from that information. Preferably, the fibrillation cycle length is determined for each fibrillation event of a given patient with continuous monitoring by the sensing electrodes so that the electrical stimulus regimen can be set according to the algorithm described herein in a real time mode, as opposed to using preselected fixed intervals. It is also possible to adjust the electrical stimulus therapy in real time during treatment as changes in the fibrillation cycle lengths are identified. The invention will be even better understood from the details provided below of several preferred embodiments of the invention.

The electrical energy used may have any suitable waveform commonly known and used in the art. The pulse delivery electrodes and related energy supply and control systems used can be of any type known in the art, e.g., of any type commonly used in implantable pacemakers. At each of the active electrodes, the characteristics of the pacing pulses can be individually controlled. They can have an amplitude of 0–10 volts and can be either monophasic (anodic or cathodic) or biphasic. Suitable pacing or pacing/sensing electrodes are generally a few square mm in area. They can be selected from active fixation type electrodes (e.g., screw-in type) passive fixation type electrodes (e.g., tined types), and/or floating type electrodes. The defibrillation electrodes are a few square cm in area. They can be selected from standard transvenous active fixation type electrodes (e.g., screw-in type), passive fixation type electrodes (e.g., tined types), and floating type electrodes that are a few cm in length (e.g., 3–7 cm) and a few French in diameter (e.g., 2–10 F). Configurations of two or more defibrillation electrodes can be used.

In general, each pacing pulse delivered by the pacing electrode can vary between 0.1 to 10 volts, the duration of each electrical pulse can be 0.03 to 3 milliseconds, and the energy of each pulse can be in the 0.01 to 50 microjoule range. The aforementioned electrical properties of the pulses are values suitable for internal administration, such as via an ICD. External administration would require significantly higher voltage levels than set forth above, as understood in the art.

The pacing train of the pacing tier of the therapy is applied for a duration of approximately 1–10 seconds. typically about 2 seconds. The pacing pulse train generally is applied once, although it can be successively repeated several more times (e.g., about 2–5 times). The pacing tier of the pacing therapy of this invention has been found to capture large regions of the ventricle, even though ventricular fibrillation is not terminated by pacing alone (as usually is the case). After delivery of pacing, then the defibrillation therapy proceeds to the second therapy tier of defibrillation shock delivery after completing pacing, as indicated in FIG. 6. That is, once capture is obtained in the low gradient region via pacing as described above, the second tier of the therapy is introduced in which a single defibrillation (VDF) shock is delivered at the end of the pacing train with a timing synchronized with the pacing rate, as described above, sufficient to terminate fibrillation.

As also indicated in FIG. 6 by the arrow extending between the CIDS enabled interrogative box (604) and the DF shock delivery box (606) that bypasses the CIDS timing box (605), if for some reason CIDS inadvertently is not enabled, a defibrillation shock will be immediately added at the end of last pacing train as a default measure. However, to achieve the maximal reductions in the energy levels for VDFT, the S1-S2 interval should be set in the above-prescribed ranges. The implementation of CIPI and CIDS can be done via hardware modifications, software modifications or a combination of hardware and software modifications.

Also, as indicated in FIG. 6, if the first pass through the pacing and defibrillation shock therapy does not achieve defibrillation, then the therapy is automatically repeated successively and interactively, as shown in FIG. 6 until the desired result is achieved.

VDF shock can be delivered using the same or different electrodes being used for pacing. However, from a practical standpoint, sensing is done with electrodes separate from the defibrillation electrodes. The VDF shocks can have monophasic or biphasic waveforms. Biphasic truncated exponential waveforms are preferred.

The VDF shocks are delivered with energy supplied at less than about 35 joules, preferably less than about 10 joules, and more preferably in a range of about 1 to 10 joules, at a delivery voltage of about 300 to 800 volts, with the duration of each VDF shock varying from about 10 to 20 milliseconds. Preferably, the aforementioned electrical properties of the VDF shocks are values suitable for internal administration, such as via an ICD. External administration would require significantly higher voltage levels than set forth above, as understood in the art. Virtually all currently available ICDs have the required power supply capacity to meet that requirement of the present invention. Also, virtually all currently available ICDs can be configured by one of ordinary skill in the art to provide the hybrid therapy with VFCL determination and pacing from a single site in accordance with the present invention.

For a standard defibrillation lead configuration of a right ventricle to superior vena cava (RV-to-SVC) lead configuration, the critical region, i.e., the low gradient region, that needs to be in the process of activation at the instant of the defibrillation shock delivery would be the apical left ventricular (LV) freewall region over the epicardium. The low gradient region in this case has an area of about 3–4 square centimeters for an average adult heart.

Also, in initiating the pacing, the trigger can also be given manually by the patient's physician (during device programming), or the trigger can be generated automatically as soon as an activation is sensed at a certain electrode according to the timing protocol described above. Similarly, at the end of the pacing train, the MPS can provide a defibrillation trigger for the delivery of the VDF therapy. The patient's physician can either enable or disable the defibrillation trigger (during device programming). Also, where the defibrillation trigger follows pacing, the CIDS can be set as a percentage of the S1-S1 interval as described above, or alternatively, the CIDS can be set to a preselected value, such as where the patient's fibrillation history is well-established.

Also, an ICD system of the present invention can be readily implemented in many patients who already need a supplemental sensing/pacing lead for biventricular pacing as placed on the LV freewall, as the same electrode used for this pacing can be used for the synchronized delivery of the defibrillation shock according to this invention.

MODE II: DEFIBRILLATION THERAPY WITH PASSIVELY-TIMED SHOCK DELIVERY

As an alternate mode of the present invention that does not employ pacing as part of the defibrillation therapy, a method of treating a heart in need of ventricular defibrillation is used that involves properly timing the delivery of the defibrillation shock to occur when a given electrophysiological state is detected as occurring in the low gradient region. This mode of the invention is practiced without resorting to any preliminary pacing treatments to precondition the low gradient region of the heart immediately before delivery of the defibrillation shock.

Figure 7:
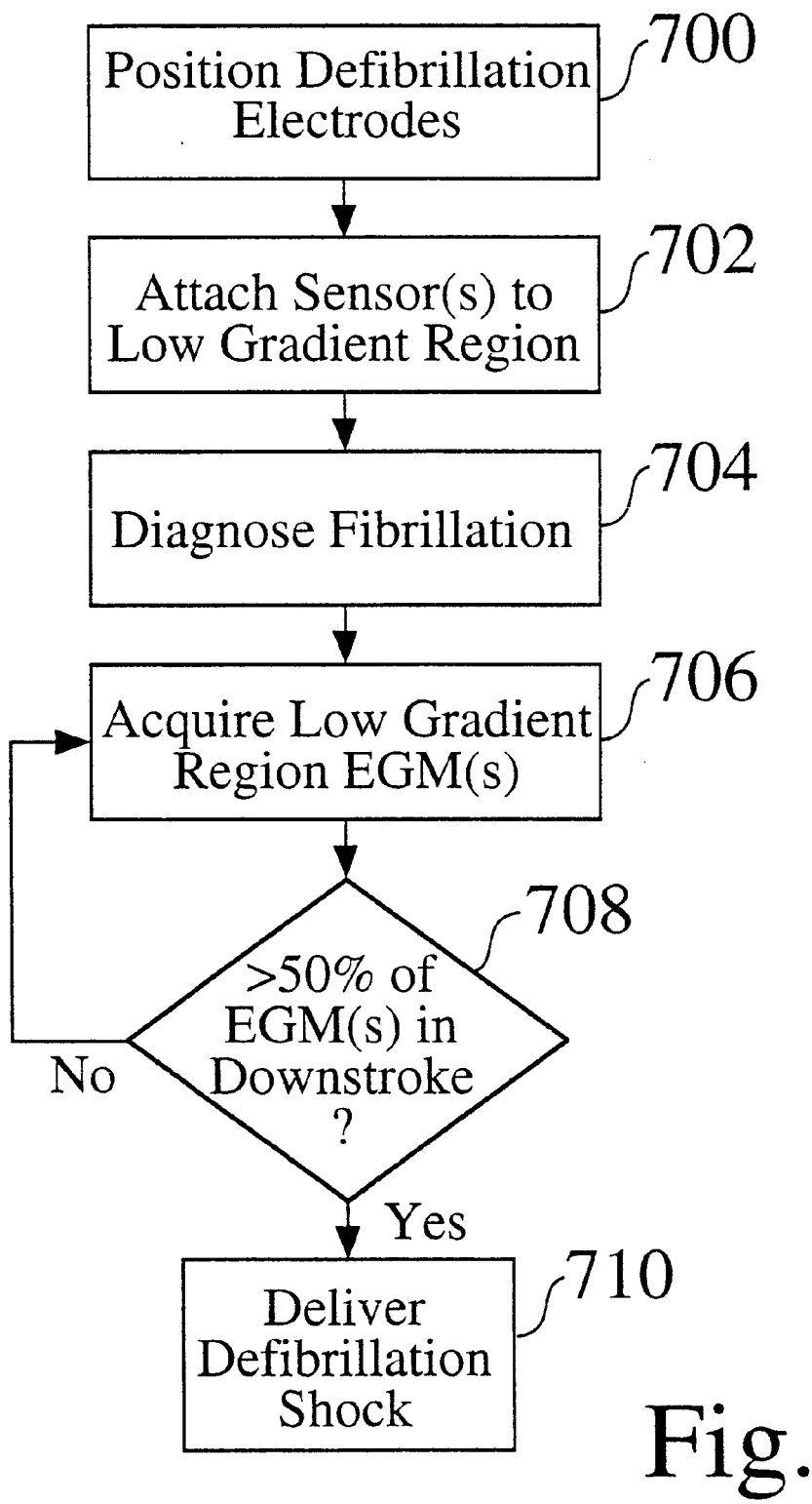
FIG. 7 is a flow chart illustrating an alternative treatment method of the present invention.

Referring now to FIG. 7, in one implementation of this mode of therapy following diagnosis of fibrillation at step 704, unipolar ventricular electrogram information is acquired at step 706 from one or more sensors attached at different sites in the low gradient region of the ventricle region of the heart at step 702, and the electrograms are monitored at step 708 until at least a majority (>50%), and preferably a substantial majority (e.g., about 80–100%). of the acquired electrograms are detected to be simultaneously in the downstroke, and then a defibrillation shock is immediately delivered to said heart at step 710 via the defibrillation electrodes positioned at step 700 effective to terminate fibrillation. The high voltage capacitor(s) of the defibrillator are charged and are at the time of the sensing of the simultaneous substantial extent of activation of the low gradient region. The substantial majority of sensed downstrokes need not all be at the exact same point of their respective downstrokes at the same time, e.g., their maximum negative slope points, as long as the various respective electrograms are all commonly somewhere on the downstroke portion of their respective EGM signals at the same instant. For this embodiment, the number of sensor locations being monitored can vary from one, to two, to three or more (e.g., 3 to 750 or even more), as long as the applicable protocols for properly timing the delivery of the defibrillation shock as taught herein are followed.

In one implementation of this mode of therapy, unipolar ventricular electrogram information is acquired from one or more sensors attached at different sites in the low gradient region of the ventricle region of the heart, and the electrograms are monitored until at least a majority (>50%), and preferably a substantial majority (e.g., about 80–100%), of the acquired electrograms are detected to be simultaneously in the downstroke, and then a defibrillation shock is immediately delivered to said heart effective to terminate fibrillation. The high voltage capacitor(s) of the defibrillator are charged and are at the time of the sensing of the simultaneous substantial extent of activation of the low gradient region. The substantial majority of sensed downstrokes need not all be at the exact same point of their respective downstrokes at the same time, e.g., their maximum negative slope points, as long as the various respective electrograms are all commonly somewhere on the downstroke portion of their respective EGM signals at the same instant. For this embodiment, the number of sensor locations being monitored can vary from one, to two, to three or more (e.g., 3 to 750 or even more), as long as the applicable protocols for properly timing the delivery of the defibrillation shock as taught herein are followed.

Figure 9:
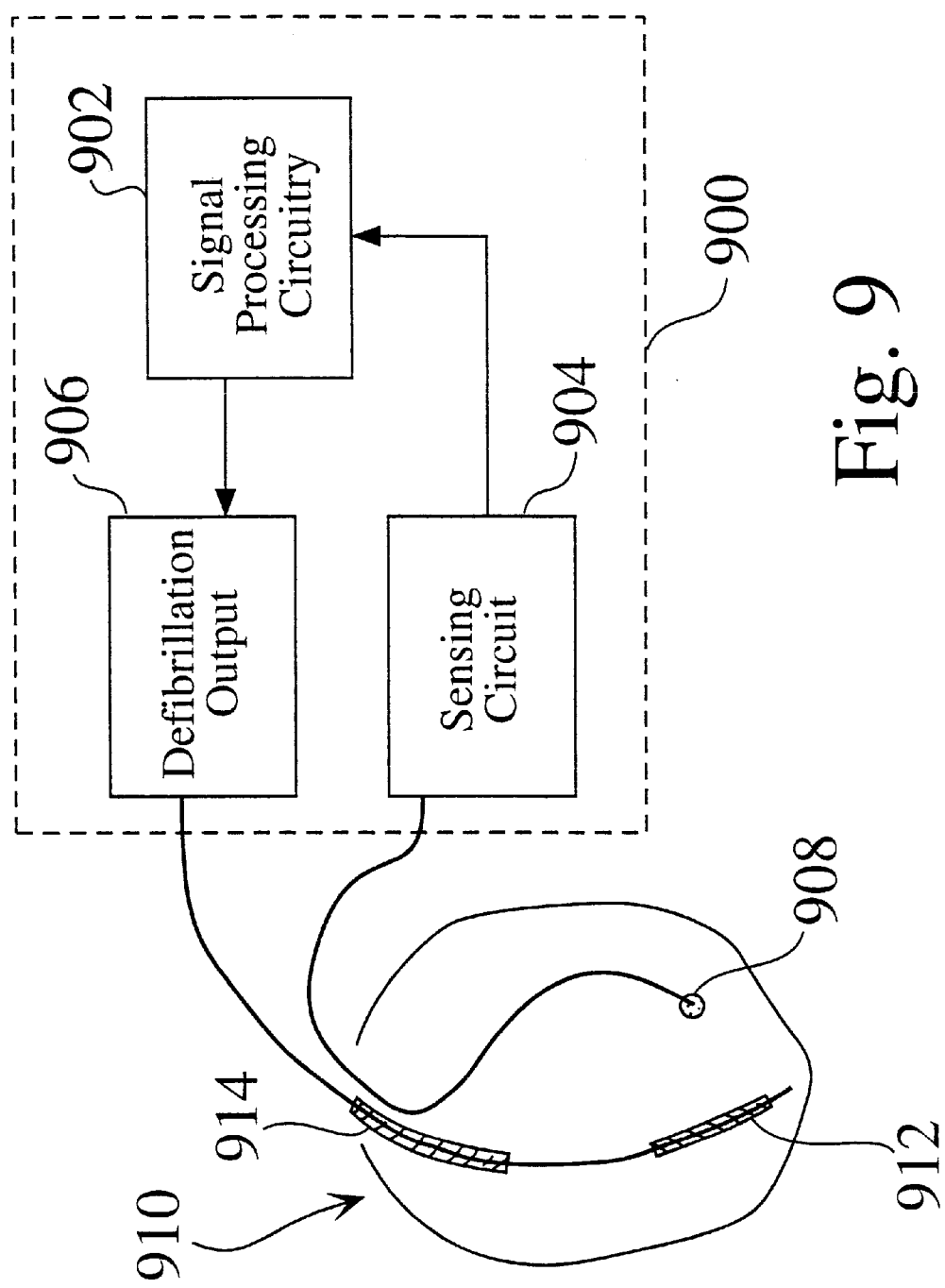
FIG. 9 is a block diagram of a defibrillation system according to the invention.

Referring now to FIG. 9, one embodiment of a cardiac therapy apparatus according to the invention is shown. A defibrillator device 900 includes signal processing circuitry 902 coupled to a sensing circuit 904 and a defibrillation output circuit 906. A sensor 908 is placed proximate the low gradient region of a patient's heart 910 and coupled to the sensing circuit 904. Defibrillation electrodes 912 and 914 are coupled to the defibrillation output circuit 906. In operation, sensor 908 is monitored in the low gradient region, then the defibrillation shock is delivered when the EGM is in the downstroke. To accomplish this. one electrogram can be inputted from the low gradient region to a pre-programmed microprocessor in signal processing circuitry 902 of a defibrillator device 900 for analysis and then the defibrillation shock is immediately delivered through defibrillation output 906 and defibrillation electrodes 912, 914 when the electrogram is determined to be on downstroke. The defibrillation shock is "immediately delivered" in the sense that the electrogram is still on the downstroke when the shock is delivered.

For instance, if one sensor is monitored in the low gradient region, then the defibrillation shock is delivered when the EGM is in the downstroke. To accomplish this, one electrogram can be inputted from the low gradient region to a pre-programmed microprocessor of a defibrillator device for analysis and then the defibrillation shock is immediately delivered when the electrogram is determined to be on downstroke. The defibrillation shock is "immediately delivered" in the sense that the electrogram is still on the downstroke when the shock is delivered.

Figure 8:
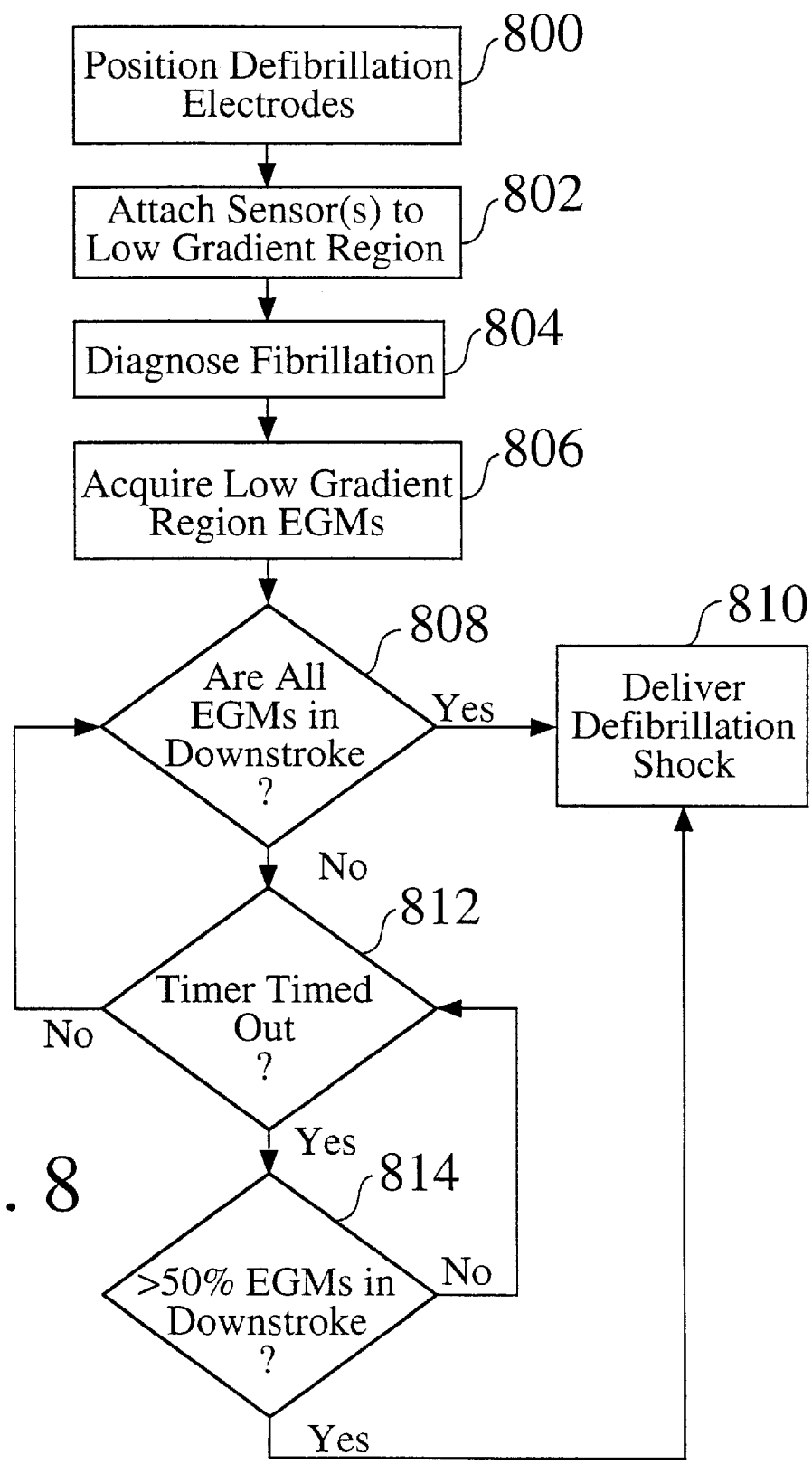
FIG. 8 is a flow chart illustrating another alternative treatment method of the present invention.

Referring now to FIG. 8, an alternative method following positioning of the defibrillation electrodes at step 800, is described. Two or more separate sensors are attached to the low gradient region at step 802 and following detection of a fibrillation episode at step 804 low gradient EGMs are acquired at step 806. Then, respective EGMs are inputted from the unipolar sensors, which can be spaced apart, for example, about 1 cm, to a pre-programmed microprocessor of a defibrillator device for analysis, and during a so-called synchronization period of, for example, about 2–4 seconds, a defibrillation shock is delivered at step 810 when and if all electrograms are simultaneously determined to be on downstroke at step 808. If the synchronization period, i.e., the initial monitoring period. elapses without that occurring as determined at step 812, then the defibrillation shock is immediately delivered the next time a majority (>50%) of the sensed sites in the low gradient region are simultaneously on downstroke as determined at step 814.

Where two or more separate sensors are monitored in the low gradient region, then respective EGMs are inputted from the unipolar sensors, which can be spaced apart, for example, about 1 cm, to a pre-programmed microprocessor of a defibrillator device for analysis, and during a so-called synchronization period of, for example, about 2–4 seconds, a defibrillation shock is delivered when and if all electrograms are simultaneously determined to be on downstroke. If the synchronization period, i.e., the initial monitoring period, elapses without that occurring, then the defibrillation shock is immediately delivered the next time a majority (>50%) of the sensed sites in the low gradient region are simultaneously on downstroke.

For a standard defibrillation lead configuration of a right ventricle to superior vena cava (RV-to-SVC) lead configuration, the critical region, i.e., the low gradient region, that needs to be in the process of activation at the instant of the defibrillation shock delivery would be the apical left ventricular (LV) freewall region over the epicardium. The low gradient region in that situation has an area of about 3–4 square centimeters, in which the sensor(s) would be located. At different times during fibrillation, different amounts of the tissue in the critical low gradient region (ranging from 0% to 100%) are in the process of activation by fibrillatory wavefronts. A finding of the present invention is that for a fixed shock strength, the probability of success of a shock is a function of the percentage of tissue in the low gradient region that is in the process of activation by fibrillatory wavefronts. When defibrillation shocks are delivered when 80–100% of the tissue in the low gradient region is in the process of activation, the probability of success is significantly improved. If all of the tissue in the low gradient region (100%) is in the process of activation, the probability of success is even higher and the voltage for defibrillation can be reduced even more.

As several practical ways to implement this technique using unipolar electrogram information and where the low gradient region is the LV freewall based on the ventricular DF lead configuration, the following exemplary arrangements can be used:

a) recording a unipolar electrogram from a sensing/pacing electrode in the great cardiac vein (via the coronary sinus) and synchronizing the defibrillation shock to occur upon detecting the downslope of the electrogram; or b) recording a unipolar electrogram from a small unipolar epicardial sensing/pacing electrode placed on the LV freewall and synchronizing the defibrillation shock to the downslope of the electrogram.

As a variation on the above technique using binary classification of the electrogram slope for timing the delivery of the defibrillation shock, it alternately is possible to generate bipolar electrogram information based on a bipolar sensing electrode configuration mounted in a low gradient region, and then timing the delivery of the DF shock to occur about 20 to 30 milliseconds after a local activation is sensed in the low gradient region. The local activation is recognized by a conspicuous "twitch" or rapid single spike movement of the bipolar electrogram from and back to a substantially flat profile. For this variant procedure using bipolar electrogram information to time the delivery of the DF shock, the following exemplary arrangements can be used:

a) recording a bipolar electrogram from a sensing/pacing electrode in the great cardiac vein (via the coronary sinus) and synchronizing the defibrillation shock to a local sensed activation; or b) recording a bipolar electrogram from an epicardial sensing/pacing electrode on the LV freewall and synchronizing the defibrillation shock to a local sensed activation.

In different implementations of Mode II of the invention using unipolar sensing, which do not involve a binary classification alone of electrogram slope for timing the delivery of the defibrillation shock, other ventricular unipolar electrogram attributes are referenced such as the amplitude of the electrogram and the magnitude of the slope of the electrogram sensed from the low gradient region during a learning period, and then at least one these parameters is used instead for timing the delivery of the defibrillation shock. Namely, another finding of the present invention is that either a relatively large amplitude or a large negative slope observed at a unipolar electrogram from the low gradient region has been found to indicate the presence of a large and rapidly moving activation wavefront over the low gradient region, which in turn indicates an increased probability of a large percentage of low gradient region tissue being on the downstroke of its EGM.

As one technique for implementing this concept, a plurality of defibrillation electrodes are first positioned in or on the heart and a sensor is positioned in the low gradient region of the ventricle. A real time unipolar ventricular electrogram is acquired from the sensor and, upon detecting a fibrillation episode, a respective real time ventricular electrogram profile history is recorded from the sensor over a given period of time as a learning period from which the largest amplitude value of the recorded electrograms for that time period is identified. A reference amplitude value is calculated as a given percentage of the largest amplitude value recorded during the learning period. Thereafter, the electrogram is monitored with amplitude values compared to the reference amplitude value until an amplitude parameter of the electrogram exceeds the reference amplitude, and then a defibrillation shock is immediately delivered to the heart effective to terminate fibrillation.

For example, once a defibrillation episode is detected, then an EGM history or profile is developed and recorded based on signals received from a sensor located in the low gradient region during the learning period, e.g., about 2–4 seconds. At the end of the learning period, a reference amplitude value is calculated as a given percentage value, e.g., about 80 to 90%, of the largest amplitude value observed and recorded during the learning period. Then, during a synchronization period, for example, about 2–4 seconds, the defibrillation shock is delivered when and if an amplitude of the current EGM being monitored in real time exceeds the reference amplitude value. and, if not, then the defibrillation shock is delivered on the next detected EGM downslope ("downstroke") period as a default measure.

As a variation of the above method, the steps are reproduced in a similar manner with the exception that upon detecting a fibrillation episode, the ensuing step of establishing and recording a respective ventricular electrogram history or profile information from the sensor in the low gradient region over a given period of time period (e.g., 2–4 seconds) is used instead for identifying the negative slope value of greatest absolute value of the recorded electrogram history information, and establishing a reference negative slope value as a given percentage (e.g., about 80–90%) of the observed and recorded negative slope value of greatest absolute value. Then, during continued monitoring with the sensor, comparisons are made of the real time negative slope values of the current electrogram with the reference negative slope value until a negative slope value is detected having an absolute value exceeding that of the reference negative slope value, and then a defibrillation shock is immediately delivered to the heart effective to terminate fibrillation. If no negative slope value exceeds the reference value within a given time period (e.g., 2–4 seconds), then the defibrillation shock is delivered on the next detected downstroke as a default measure.

By immediately delivering the defibrillation shock when the magnitude of the downstroke is sensed to be relatively large in amplitude or negative slope value results in a increased probability of success of defibrillation. Moreover, there exists an increased probability of a lower VDFT being exploitable at that time.

Suitable sensing electrodes, defibrillation electrodes, signal processing equipment, and other support equipment for practicing these embodiments of Mode II include the equipment described above in connection with Mode I. Similarly, the energy, voltage, and durational properties of the DF shocks useful for the embodiments of Mode II are the same as those described above in connection with Mode I.

The following experiments were conducted which illustrate aspects of the invention. The experiments are not intended to limit the scope of the invention in any respect and should not be so construed.

EXPERIMENTAL

Example 1

Animal Preparation

Eight mongrel dogs, each weighing 18–25 kg, were studied. After an IV was established, the anesthesia utilized was a bolus of pentobarbital 30–35 mg/kg IV followed by a continuous 0.05 mg/kg/min. IV drip and supplemented with morphine sulfate 0.4 mg/kg IM followed by boluses of 0.2 mg/kg every 2 hours. The animals were intubated with a cuffed endotracheal tube and repirated through a Drager ventilator (model SAV, Telford, Pa., USA). Arterial blood pressure was monitored using a femoral catheter that was placed via a cut down or percutaneous. Body surface ECG leads were positioned appropriately and continuously monitored. IV maintenance fluids with Lactated Ringers solution were started. Body temperature was monitored and was maintained using an electrical blanket. Electrolyte concentration and respirator rate modifications were adopted as needed depending on serial electrolyte and arterial blood gas measurements. To reduce muscle contraction induced by defibrillation shocks, succinylcholine was given at 1 mg/kg IV bolus, and then as needed but no more than once per hour at 0.25 to 0.5 mg/kg.

Electrode Placement

Each test animal was placed on its left side and the implantation of a superior vena cava (SVC) lead and a RV lead (St. Jude Medical CRMD, Sunnyvale, Calif., USA) was performed under fluoroscopy via the right external jugular vein. The coil length of the SVC defibrillation electrode was 7.2 cm with an 8.5-French diameter. The coil length of the RV defibrillation electrode was 5.0 cm with a 9-French diameter. The pacing/sensing electrode, located at the distal tip of the RV lead, was made of high surface area sintered platinum. For the electrode configuration used in this study, the low gradient region was the LV apex and LV lateral freewall. See, e.g., Pendekanti R., et al., "Epicardial mapping and defibrillation thresholds using an endocardial lead in the left ventricle," PACE. 1997;20[Pt.II]:1115; Tang A., et al., "Three-dimensional potential gradient fields generated by intracardiac catheter and cutaneous patch electrodes," Circulation. 1992;85: 1857–1864; and Wolf P., et al., "Epicardial mapping demonstrates a predictable arrhythmia following unsuccessful transvenous defibrillation near threshold," J Am Coll Cardiol. 1994;23:421A. The electrograms recorded from this low gradient region contained information regarding the electrical state of the myocardium in their proximity, with the downstroke indicating local activation. Local activation under a recording extracellular electrode has been defined as the time instant when the upstroke of the transmembrane potential (TMP) is a maximum. See, e.g., Ideker R., et al., "The assumptions of isochronal cardiac mapping," PACE. 1989;12:456–478. The local activation in the low gradient region thus occurs during the downstroke of the local unipolar electrogram at the instant of maximum negative slope.

To minimize pull-back of the RV catheter, positioning of the lead in the RV apex was guided by two fluoroscopic views: AP and RAO caudal 25°, such as described in more detail by Usui, M., et al., "Influence of malpositioned transvenous leads on defibrillation efficacy with and without a subcutaneous array electrode," PACE. 1995;18:2008–2016, and Lang, D., et al., "Implantable cardioverter defibrillator lead technology: improved performance and lower defibrillation thresholds," PACE. 1995; 18:548–559.

A median sternotomy was performed to open the chest so that a 525-channel sensing electrode elastic sock could be applied to the epicardial surface. There were 18 rings of Ag/AgCl unipolar sensing electrodes on the sock from apex to base, the number of electrodes on each ring were 6, 7, 11, 14, 21, 24, 28, 32, 34, 36, 38, 38, 41, 41, 42, 42, 36, and 34, respectively. Each electrode was about 1 mm in diameter. The center-to-center spacing between neighboring electrodes was approximately 4 mm. The heart was placed in the pericardial cradle and the sock was pulled over it such that the LV apex was in contact with the apical electrodes and the base of the sock was about 1 cm above the AV groove. The sock was sutured to the pericardium where available and to the epicardium elsewhere. The chest retraction was then removed from the sternum.

Defibrillation Protocols

The defibrillation leads were connected to an external defibrillator (viz., model HVS-02, St. Jude Medical CRMD, Sunnyvale, Calif., USA) programmed to deliver a biphasic waveform with a first phase of fixed tilt from a 150 $\mu F$ capacitance and a second phase of fixed tilt from a 300 $\mu F$ capacitance. The leading edge of the second phase had approximately one-half the magnitude and was opposite in polarity to the trailing edge of the first phase.

Before defibrillation testing, the R wave amplitude, pacing lead impedance, and pacing thresholds at 0.5 and 1 msec pacing pulse widths were measured from the RV tip. Next, a R-wave synchronous biphasic shock (500V, 14 msec) was delivered to estimate the defibrillation lead impedance. Based on this estimate, the pulse width of the subsequent shocks was set to the suggested value from the HVS-02 Operator's Manual. For defibrillation testing, the ventilator was switched off and a 50 Hz burst pacing at 10 V was delivered via the RV tip to induce VF. Defibrillation shocks were delivered after 10 seconds of VF. Following an unsuccessful defibrillation attempt, a high-voltage rescue shock was delivered. The ventilator was switched on immediately after defibrillation. VF/DF trials were performed every 3 minutes.

The 50% successful defibrillation voltage threshold value was estimated using a three reversal up/down protocol. This protocol is describe in more detail by Gill, R., et al., "The defibrillation threshold: A comparison of anesthetics and measurement methods," PACE. 1993;16:708–714, and Daniel, W., et al., "An up-down algorithm for estimation of the cardiac defibrillation threshold," Med Instrum. 1988;22:286–292. The first test shock was delivered at 600 V. The test shock was incremented by 50 V after a failure and decremented by 50 V after a success. The first test shock failure after a test shock success was counted as the first turning point. The next successful test shock was the second turning point. The next failed test shock was the third turning point. The next successful test shock was the forth turning point. Voltages of all the test shocks applied from and including the first turning point until and including the forth turning point were averaged to estimate the 50% successful defibrillation voltage threshold value (V50) and the corresponding energy threshold (E50).

Starting at the V50, 20 to 50 test shocks were delivered during fibrillation in pairs (10 to 25 pairs). If both shocks in a pair failed, the voltage of the next pair was increased by 10 V. If both shocks in a pair succeeded, the voltage of the next pair of shocks was decreased by 10 V. If one shock in a pair succeeded and the other failed, the next pair of shocks was delivered at the same voltage level. This protocol was used so that the voltage of the applied shocks tracked any changes in the V50 with time.

Data Processing and Analysis

The unipolar signals from each of the 525 epicardial electrodes were entered into a computer-assisted mapping system capable of simultaneous recordings from 528 channels. This system is described in more detail by Wolf P., et al., "A 528 channel system for the acquisition and display of defibrillation and electrocardiographic potentials," Comput Cardiol. 1993.

The other three channels were used to record the unipolar electrograms from the endocardial pacing/sensing RV tip electrode, the defibrillation RV coil electrode, and the defibrillation SVC coil electrode. The unipolar electrodes were connected to the positive side of the amplifiers and ground was connected to the negative side of the amplifier. The recordings were filtered with a 0.5 Hz high-pass filter and a 500 Hz low-pass filter and recorded digitally at 2000 samples per second per channel using a workstation (Sun Microsystems, Mountain View, Calif., USA) and backed up on a magneto-optical disk (Pinnacle Micro, Irvine, Calif. USA). This data was collected from the initiation of VF until 5 msec before the defibrillation shock was applied.

At the completion of the defibrillation protocol, the electrogram data were analyzed retrospectively. At each electrode and for each test shock, the slope of the electrogram (dV/dt) just before the test shock was computed. The dV/dt was determined by fitting a parabola to the last five data points pre-shock (spanning 2 msec). The electrogram morphology at each electrode just before each test shock was classified as being either on the up-slope, i.e., upstroke, where dV/dt>0, or on the down-slope, i.e., the downstroke, where dV/dt<0. Next, for each electrode the percentage of shocks on the upstroke that successfully defibrillated (PUp) and the percentage of shocks on the downstroke that successfully defibrillated (PDn) were computed. If PUp>PDn, shock on upstroke was more efficacious for that electrogram. If PDn>PUp, shock on downstroke is more efficacious for that electrogram.

The significance of the differences were determined using Student's paired t-tests and Chi-square tests and were considered significant at p<0.05.

Results

For the eight dogs studied, the V50 was 550±170 V, the E50 was 17.4±7.8 J, and the defibrillation impedance was 58.6±3.3 Ω. A total of 220 VF/DF episodes were analyzed.

Figure 2:
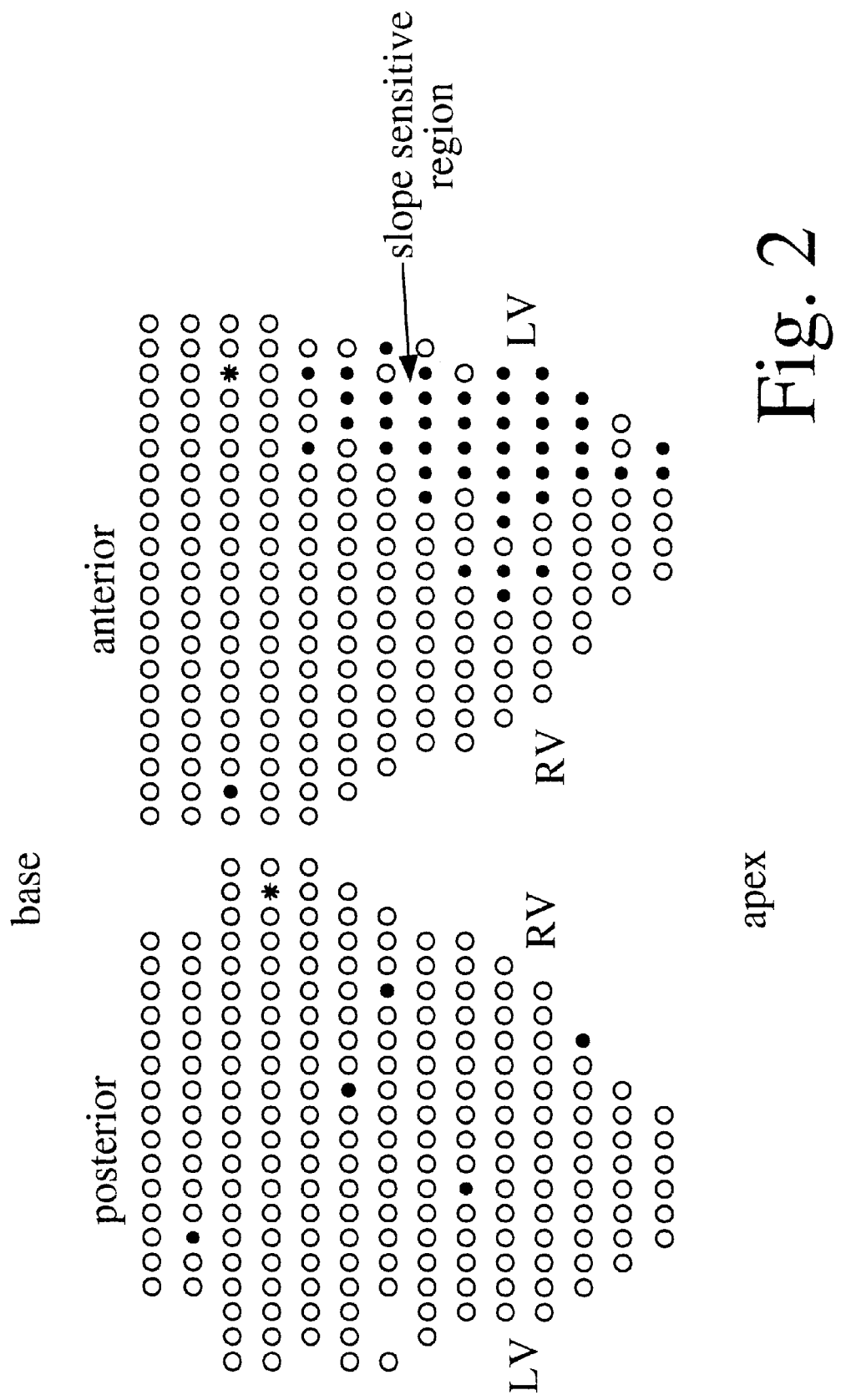
FIG. 2 shows a schematic of the electrode distribution on the ventricular epicardium for VF/DF episode and therapy that is described in experimental section of this application.

In FIGS. 1A and 1B, two of the 528 unipolar electrograms recorded simultaneously from one VF/DF episode are shown. VF was allowed to go on for 10 seconds at which time a successful defibrillation shock was delivered. The location (1) of "electrode #1" is indicated in FIG. 2. As seen from FIG. 1A, the electrogram from electrode 1 was on the downstroke at the instant the shock was delivered. So with respect to that electrode location, that shock was classified as "downstroke". However, for the electrogram from electrode 5 (FIG. 1B), the shock was delivered on the upstroke. The location (5) of "electrode #5" is indicated in FIG. 2. So with respect to that electrode location, that shock was classified as "upstroke". Therefore the same shock could be classified as a "upstroke" shock for some electrodes and as a shock on "downstroke" shock for the remaining electrodes.

For all electrograms, the downstroke was far more rapid than the upstroke. On average, during VF, electrograms spent 68±5% of time on the upstroke and 32±6% of time on the downstroke. Just before the shock was delivered, on average there were 34±6% of electrograms on the downstroke and the rest on upstroke. For the failed shocks there were 31±9% of the electrograms on the downstroke and the rest on the upstroke. For the successful shocks there were 37±8% of the electrograms on the downstroke and the rest on upstroke. There was no statistically significant difference in the percentage of shocks on the downstroke for successful shocks when compared to failed shocks (i.e., 37±8% vs. 31±9%, p=0.19).

The comparisons between PDn and PUp for various endocardial leads are listed in Table 1. In Table 1, "PDn" is the percentage of shocks delivered on the downstroke of electrogram that were successful, and "PUp" is the percentage of shocks delivered on the upstroke of electrogram that were successful.

TABLE 1

| Endocardial electrograms | | |
|---|---|---|
|  | PDn | PUp |
| RV tip | 48 ± 3% | 56 ± 8% |
| RV coil | 49 ± 7% | 53 ± 5% |
| SVC coil | 53 ± 9% | 47 ± 2% |
| RV tip to SVC coil | 49 ± 6% | 55 ± 4% |
| RV tip to RV coil | 47 ± 5% | 55 ± 6% |
| RV coil to SVC coil | 53 ± 6% | 49 ± 8% |

As seen from the results of Table 1, for shock timing based on slope of the unipolar electrogram from the RV tip, there is no significant difference observed. Similarly there were no significant differences using the unipolar RV coil electrogram, unipolar SVC coil electrogram, the RV-tip to SVC coil electrogram, and the RV-tip to RV-coil electrogram, or the RV-coil to SVC coil electrogram.

FIG. 2 shows the results of the analysis for the epicardial electrodes. Out of the 525 electrodes placed epicardially, some of those located on the atrial epicardium are not shown in FIG. 2 ("LV" means the left ventricle and "RV" means the right ventricle). Electrode locations shown with solid-filled circles are electrode locations where the 'percentage of shocks delivered on the downstroke of the local electrogram that are successful (PDn)' is significantly greater than the 'percentage of shocks that are delivered on the upstroke of the local electrogram that are successful (PUp)'. The low gradient region is defined to encompass the subset of these electrodes where ≧50% of the neighboring electrodes also have PDn significantly greater than PUp. Electrode locations shown with unfilled circles are where is there is no significant difference. The two electrode locations shown with asterisks "*" have PUp significantly greater PDn.

Also, as shown from the results listed in Table 2 below, the shock outcome is significantly correlated to the electrogram slopes within (and only within) this low gradient region.

TABLE 2

| Epicardial Electrograms | | |
|---|---|---|
|  | PDn | PUp |
| Slope sensitive region | 70 ± 6% | 39 ± 4% |
| Rest of epicardium | 48 ± 4% | 52 ± 8% |

As seen from FIG. 2 and the results in Table 2, there exists a low gradient region over the anterior LV free wall for which the outcome of the shock is well correlated with the slope of one or more local unipolar electrograms. For shocks of the same strength (equal to the V50 of random shocks applied after 10 seconds of fibrillation). the percentage of success depends significantly on the slope of the local unipolar electrogram. Shocks delivered on the local downstroke had increased the probability of success to 70%, while shocks delivered on the local upstroke had reduced the probability of success to only 39%. This indicates that the V50 for shocks applied randomly is equivalent to the V70 when the shock is delivered during the downstroke and to the V39 when the shock is delivered during the upstroke. This suggests that the probability of success at a given shock strength can be effected by 31% (70% minus 39%) by timing the shock on the basis of slope of an electrogram from the low gradient region alone.

The results obtained in this study have shown that, instead of increasing the defibrillation voltage, the probability of success at a given shock strength can be increased from 50% (for random shocks) to 70% by delivering the shock on the downstroke of an electrogram from the slope sensitive region. Therefore delivering the shock on the downstroke of a low gradient region electrogram has the same effect as increasing the voltage by 9%. In other words, this is a 9% improvement in the voltage DFT. Since the energy is proportional to the square of the voltage, this will be a 17% improvement in the energy DFT.

Figure 5A:
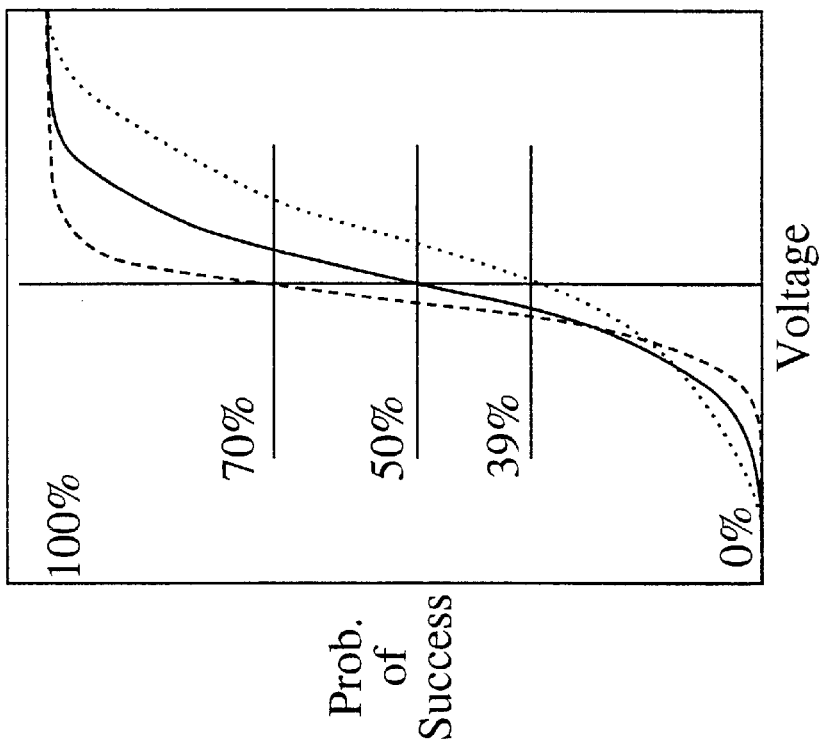
FIG. 5A shows schematics showing possible effects of shock timing on the sigmoidal probability of success curves.
Figure 5B:
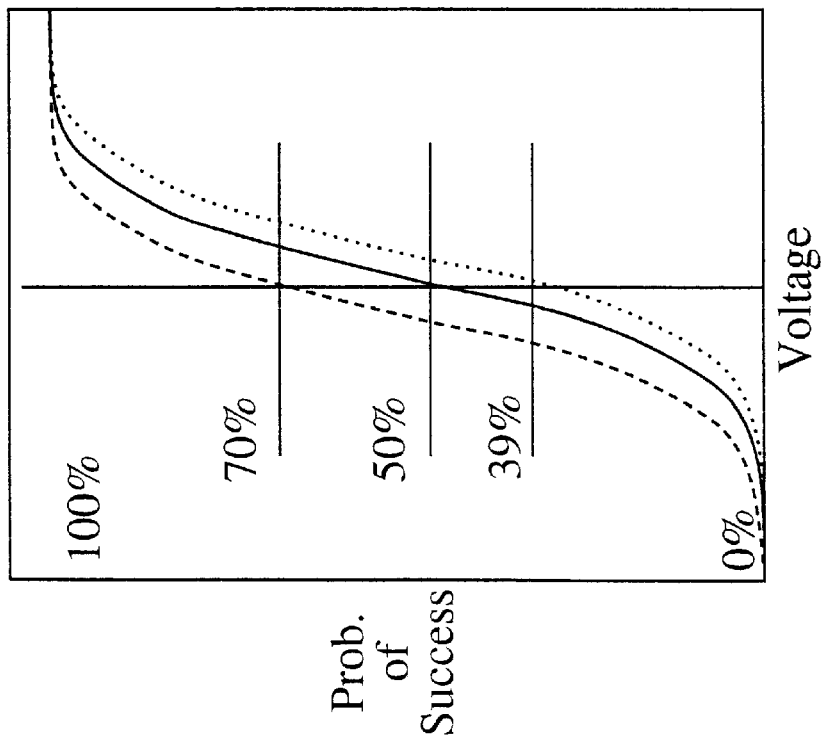
FIG. 5B shows a schematic of possible effects of shock timing on the sigmoidal probability of success curves that shock timing can also effect the slope of the curve in addition to translating the sigmoidal curve along the x-axis.

Another way of interpreting the finding is that the probability of success curve for timing a shock to the downstroke is different from, and is located to the left of, the probability of success curve for shocks timed to the upstroke of an electrogram from the slope sensitive region, as illustrated in FIG. 5A. As shown by FIG. 5A, shock timing can translate the sigmoidal curve along the x-axis. The dashed sigmoidal curve corresponds to shock on downstroke of electrogram from the slope sensitive region. The dotted sigmoidal curve corresponds to shock on upstroke of electrogram from the slope sensitive region. The solid sigmoidal curve is the weighted average of the upstroke and downstroke curves and corresponds to the random shocks. Since electrograms spend about 69% of the time on the upstroke and about 31% of the time on the downstroke, the weight of the probability of success curve for shocks timed to the upstroke should be 0.69 and the weight of the probability of success curve for shocks timed to the downstroke should be 0.31. In addition to shifting the probability of success curves to the right or left, shock timing can also influence the steepness of the curve, as illustrated in FIG. 5B.

This study by the present inventors shows that each of the unipolar ventricular electrograms recorded spends less than a third of the time on the downstroke. There can be two periods of activity defined while the electrogram is on the downstroke: (1) the time preceding the instant of maximum downward slope, when depolarization by the next fibrillatory wavefront will soon occur, or (2) the time following the instant of maximum downward slope, when depolarization by fibrillatory wavefronts has just occurred. In the case of an electrogram recorded from an electrode located over the low gradient region, if the shock falls in the first period the tissue around the recording electrode will be late in the repolarization state and so will be more likely to be directly excited by the shock, thereby directly contributing to the critical mass of defibrillation and increasing the probability of successful defibrillation. If the shock falls in the second period the tissue around the recording electrode will be in a state of absolute refractoriness when the shock is delivered. Therefore, activation fronts can not propagate from the directly excited regions to the low gradient region where the electrogram is being recorded. Hence in both cases, shocking on the downstroke can assist in increasing the probability of successful defibrillation at a given test shock intensity.

Figure 3:
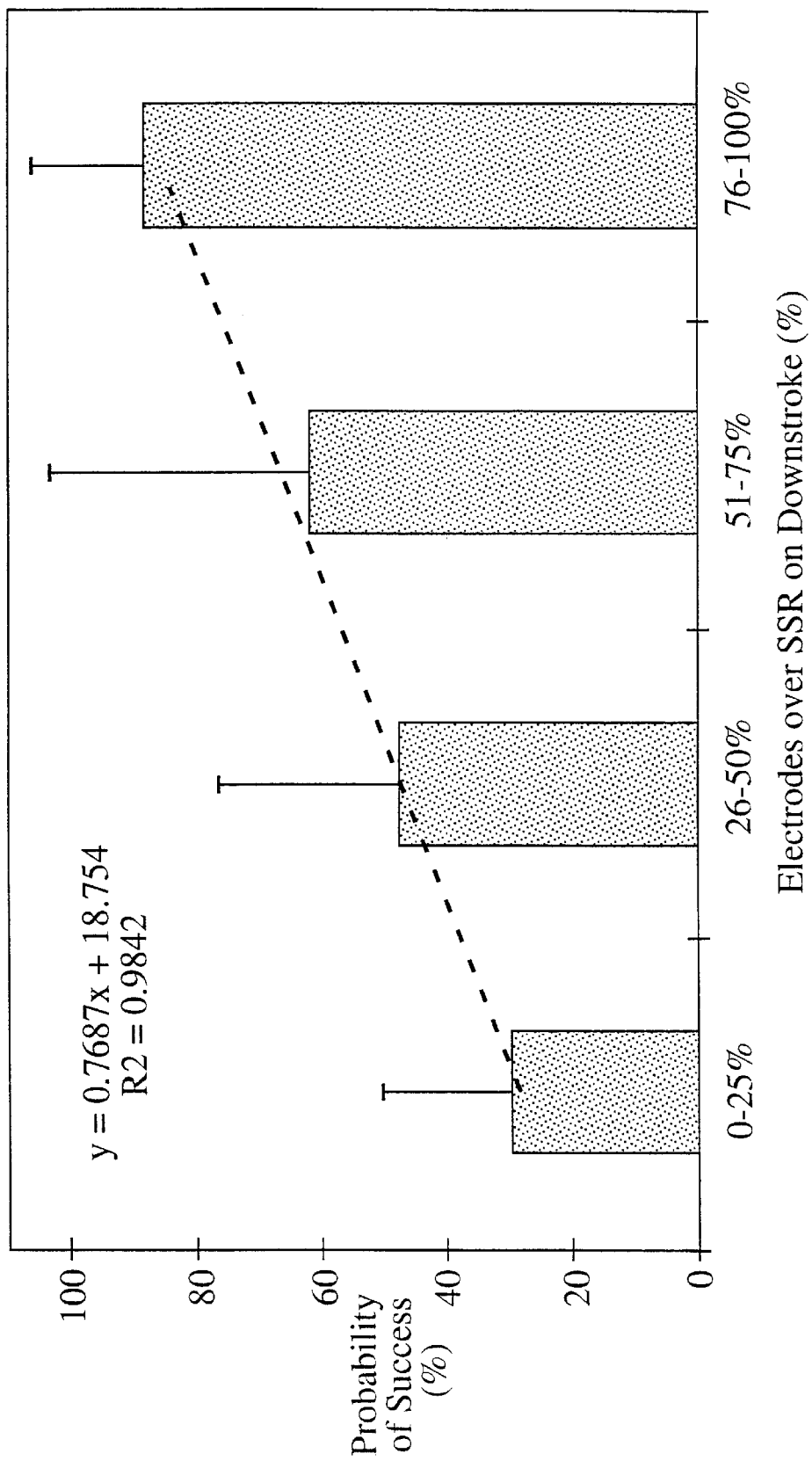
FIG. 3 shows a histogram of the probability of successful defibrillation as a function of the percentage of the electrograms acquired from multiple sites of the low gradient region ("LGR") that were on the downstroke at the time of defibrillation shock delivery.

Also, for each defibrillation shock delivered, the percentage of electrograms from the low gradient region that were on the downstroke when the shock was delivered was determined. FIG. 3 shows the histogram showing the probability of success as a function of the percentage of electrograms from the low gradient region that were on the downstroke when the shock was delivered. Histograms were first obtained for each of eight animals studied and then averaged. The bars indicate the standard deviation. The probability of success is seen to increase linearly as the percentage of low gradient region electrograms on the downstroke increases. The probability of success of the V50 shocks was significantly higher when the percentage of electrograms from the low gradient region that were on the downstroke when the shock was delivered was 76%–100% as compared to 0–25% (88.9±17.2% vs. 29.7±20.2%, p<0.02) and as compared to 26–50% (88.9±17.2% vs. 62.4.7±41.0%, p<0.03). The correlation coefficient of linear regression ($R^2$) is better than 0.98.

As a control to the low gradient region analysis results shown in FIG. 3, a region similar in size to the low gradient region was selected on the right ventricular free wall and the above experimental analysis was repeated with the results being illustrated in FIG. 4. This region was diametrically opposite the low gradient region and was a high gradient region. This figure is provided to illustrate that the findings obtained by using the low gradient region electrograms may be unique to that region alone and may not be obtained for other similar size regions (such as the one used here). As seen from FIG. 4, there was no significant difference in the probability of success as a function of the percentage of electrograms from the RV free wall region that were on the downstroke when the shock was delivered.

Based on experimental findings reported in FIGS. 3 and 4, it was clearly shown that the probability of success of a defibrillation shock depends on the percentage of low gradient region electrograms that are on the downstroke in the low gradient region when the shock is delivered. If more of these electrograms are on their downstroke, then a shock is more likely to succeed.

Using the regression equation y=0.7687X+18.754 (where R2=0.9842), which plots the data in FIG. 3, it is possible to estimate that when 0% of low gradient region electrograms are on downstroke, then the probability of success is approximately 19%. Similarly when 100% of the low gradient region electrograms are on downstroke, then the probability of success is 95%. Now it can be seen that this accounts for 76% (95% minus 19%) of the variability in the probability of success, and that the V50 shock behaves like a V95 shock when timed such that 100% of the low gradient region electrograms are on downstroke. In line with the previous estimates, using (V80–V50)/V50=0.14, such as reported by Souza J., et al., "Comparison of upper limit of vulnerability and defibrillation probability of success curves using a nonthoracotomy lead system," *Circulation.* 1995;91:1247–1252, (V95–V50)/V50=0.21 is arrived at by linear approximation. Therefore delivering the shock when 100% of the low gradient region electrograms are on downstroke, increases the probability of success by the same amount as increasing the voltage by 21%. This can be considered to be a 21% reduction in the voltage DFT and corresponding 38% decrease in the energy DFT. It should be noted that this is only an approximation because it is known that the probability of success curve is not linear in the V95 region.

If approximately 100% of the low gradient region electrograms are on the downstroke, it means that there should be at least one fibrillatory wavefront on the low gradient region that is in the process of activating the whole low gradient region. This is not a common occurrence. It has been found during fibrillation, the total time when ≧90% of the low gradient region electrograms are on downstroke is less than 2% during the first 10 seconds of fibrillation.

A practical implication of this study is revealed by examining the anatomical location over which the slope sensitive region is observed. This region is located on the LV anterior free wall. This is a region over which some of the cardiac veins are located. The left sided pacing electrode for such pacing can be implanted via the CS into the cardiac vein. The electrogram from the same electrode can also be used for shock timing based on the slope or local activation as described in the present application. Moreover, since patients with chronic heart failure (CHF) tend to have enlarged LV and therefore higher DFTs, these are also the patients who are most likely to benefit the most by timing the shock appropriately to the local electrogram.

Shock timing based on the binary classification of slope (as being either positive or negative) has been shown in the experimental studies reported herein to reduce the energy DFT by 17%. It has also been shown that the energy DFT can further reduce as the percentage of the low gradient region electrograms that are the downstroke increases. In another mode of the invention, one way to time the shock for increased probability of success is to record electrograms from more than one low gradient region electrode and to deliver the shock when all these electrograms are on the downstroke. In another mode, in addition to the binary classification of slope, it is possible to additionally consider other quantities like the amplitude of the low gradient electrogram and the magnitude of the slope. A large amplitude and a large negative slope observed at an low gradient region electrogram is thought to indicate the presence of a large and rapidly moving activation wavefront over the low gradient region which in turn should result in a large percentage of low gradient region to be on the downstroke. Therefore delivering the shock when the magnitude of the downstroke is large also should result in a increased probability of success.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A method for delivering defibrillation therapy to a patient's heart comprising the steps of:

(a) positioning a defibrillation electrode in the right ventricle and a defibrillation electrode in the superior vena cava;

(b) attaching a sensor in a low gradient region comprising the left ventriclar free wall region;

(c) acquiring real time ventricular unipolar electrogram signals from said sensor and detecting a fibrillation episode in said patient's heart;

(d) upon detecting a fibrillation episode during step (c), establishing a real time ventricular electrogram history based on unipolar electrogram signals acquired from said sensor for a first period of time and identifying the largest amplitude value of the established electrogram history, and establishing a reference amplitude value based as a percentage of said largest amplitude value;

(e) monitoring said electrogram over a second period of time to detect for a first condition in which an amplitude parameter of the electrogram exceeds said reference amplitude value;

(f) delivering a defibrillation shock to said heart fibrillation immediately upon an occurrence of said first condition during said second period of time, effective to terminate fibrillation;

(g) continuing monitoring said electrogram to detect for a second condition in the event said second period of time elapses without the occurrence of said first condition, wherein the second condition occurs when the electrogram is monitored to be in downstroke; and (h) delivering a defibrillation shock to said heart fibrillation immediately upon the occurrence of said second condition, effective to terminate fibrillation.

2. The method of claim 1, wherein said percentage in step (d) is about 80–90%.

3. The method of claim 1, wherein said first period of time is about 2–4 seconds.

4. The method of claim 1, wherein said second period of time is about 2–4 seconds.

* * * * *